United States Patent [19]

Sakazume et al.

[11] Patent Number: 5,670,114
[45] Date of Patent: Sep. 23, 1997

[54] APPARATUS OF HANDLING REAGENT FOR SUPPRESSING DECREASE IN EFFECT OF REAGENT

[75] Inventors: Taku Sakazume, Hitachinaka; Hiroshi Mitsumaki, Mito; Katsuaki Takahashi; Terumi Tamura, both of Hitachinaka, all of Japan

[73] Assignee: Hitachi, Ltd., Tokyo, Japan

[21] Appl. No.: 608,564

[22] Filed: Feb. 28, 1996

[30] Foreign Application Priority Data

Mar. 8, 1995 [JP] Japan ................................. 7-048090

[51] Int. Cl.$^6$ .................................................. G01N 35/00
[52] U.S. Cl. ............................ 422/67; 422/63; 422/64; 422/100; 422/101; 422/104; 436/43; 436/47; 436/50; 436/55; 436/175
[58] Field of Search .......................... 422/63, 64, 67, 422/68.1, 100, 101, 104; 436/43, 47, 50, 55, 174, 177, 160, 175

[56] References Cited

U.S. PATENT DOCUMENTS

| | | | |
|---|---|---|---|
| 3,901,656 | 8/1975 | Durkos et al. | 422/64 |
| 4,455,280 | 6/1984 | Shinohara et al. | 422/63 |
| 5,039,614 | 8/1991 | Dekmezian et al. | 436/43 |
| 5,051,238 | 9/1991 | Umetsu et al. | 422/64 |
| 5,156,809 | 10/1992 | Hupe et al. | 422/64 |
| 5,171,531 | 12/1992 | Christianson et al. | 422/64 |
| 5,343,770 | 9/1994 | Seidoh et al. | 73/864.22 |

FOREIGN PATENT DOCUMENTS

| | | |
|---|---|---|
| 4-305157 | 10/1992 | Japan. |
| 4-326063 | 11/1992 | Japan. |

OTHER PUBLICATIONS

JJCLA, vol. 16, No. 2, 1991, "Enzymatic Assay of Serum Total C02 in Air", Yamamoto et al, pp. 121–125.

*Primary Examiner*—Long V. Le
*Attorney, Agent, or Firm*—Fay, Sharpe, Beall, Fagan, Minnich & McKee

[57] ABSTRACT

An analyzer for chemically analyzing biological samples delivers required reagents in a plurality of reagent bottles to reaction containers corresponding to analysis items. A reagent which becomes deteriorated by carbonic acid gas is registered in advance, and it is judged by a control device whether such a reagent bottle is loaded in the reagent containing chamber or not. If such a reagent bottle is loaded in the reagent containing chamber, a purge gas for sweeping-out air containing carbonic acid gas is supplied to the reagent containing chamber. The flow rate of the purge gas is controlled so as to be large during an initial period of analysis preparation stage and is then decreased.

6 Claims, 5 Drawing Sheets

APPARATUS OF HANDLING REAGENT FOR SUPPRESSING DECREASE IN EFFECT OF REAGENT

BACKGROUND OF THE INVENTION

The present invention relates to a method of handling reagents and an apparatus thereof and, more particularly, to a method of handling a reagent and an apparatus thereof suitable for reagents which are quickly deteriorated by carbonic acid gas in atmospheric air during the analyzing of biological samples.

Analysis of various kinds of components contained in a biological sample such as blood or urine gives valuable information for diagnosing patient's disease. An automated analyzing apparatus of this kind is disclosed, for example, in Japanese Patent Application Laid-Open No. 4-326063 (1992). In this prior art, there is described an example where a sample and a reagent are delivered in a reaction container, and the reaction liquid is measured using a photometer. Each of the two reagent rerigerators of the analyzing apparatus has a movable holder on which many reagent bottles are placed. The kind of each reagent can be identified by reading the bar code marked on the reagent bottle.

Among various kinds of analyzing items, some items have to use a reagent which rapidly changes its composition by contacting with atmospheric air. One of the example is described in JJCLA; vol. 16, No. 2, pp 121–125 (1991). It is described that in a case where carbonic acid gas contained in blood serum is measured by an enzymatic method, a solution containing phosphoenol-pyruvate is used as a first reagent. Further, this prior art teaches that the reagent is bubbled through nitrogen gas in order to prevent carbonic acid gas from dissolving into the reagent.

Another example of method for reducing deterioration of a reagent is disclosed in Japanese Patent Application Laid-Open No. 4-305157 (1992), where a sample containing an organic chlorine compound is mixed with biphenyl sodium to produce chloride ions, and concentration of the chloride ions is measured using a liquid chromatograph. The prior art teaches that in order to isolate the reagent containing biphenyl sodium from air, the reagent bottle is stored in a box filled with nitrogen gas as an inert gas.

Since analysis items analyzed using a clinical analyzer cover various kinds, a lot of reagent bottles containing reagents having various properties are contained in a single reagent containing chamber to be used for multi-item analysis. Among reagents to be used, there are some reagents whose effect is deteriorated by carbonic acid gas and some reagents which requires oxygen. However, either in JJCLA; vol. 16, No. 2, pp 121–125 (1991) and in Japanese Patent Application Laid-Open No. 4-305157 (1992), it is not considered that a lot of reagents used for measurement of multi-analysis items are contained in a single reagent containing chamber. In addition to this, only nitrogen gas is described as a gas for suppressing deterioration in the effect of the reagents described in the materials of the prior art.

SUMMARY OF THE INVENTION

An object of the present invention is to provide a method of handling reagents and an apparatus thereof which are improved so as to not uselessly consume purge gas for suppressing deterioration in the effect of the reagents due to carbonic acid gas in atmospheric air.

Another object of the present invention is to provide a method of handling reagents and an apparatus thereof in which the supply of the purge gas is controlled by automatically judging whether or not it is necessary to supply the purge gas to a reagent containing chamber.

In the present invention, purge gas for sweeping out air containing carbonic acid gas is supplied to the reagent containing chamber. Information on a reagent affected by carbonic acid gas or information on an analysis item using the reagent is registered in a control device in advance. Reagent information on reagent bottles contained in the reagent containing chamber or information on analysis items corresponding to the reagents is checked against the aforementioned information, and the control device judges whether the corresponding reagent bottle is contained or not. After it is judged that the corresponding reagent bottle is contained and the reagent containing chamber is brought to a substantially sealed state, the purge gas is supplied into the reagent containing chamber from a gas supply device.

DETAILED DESCRIPTION OF THE PREFERRED EMBODIMENTS

Figure 1:
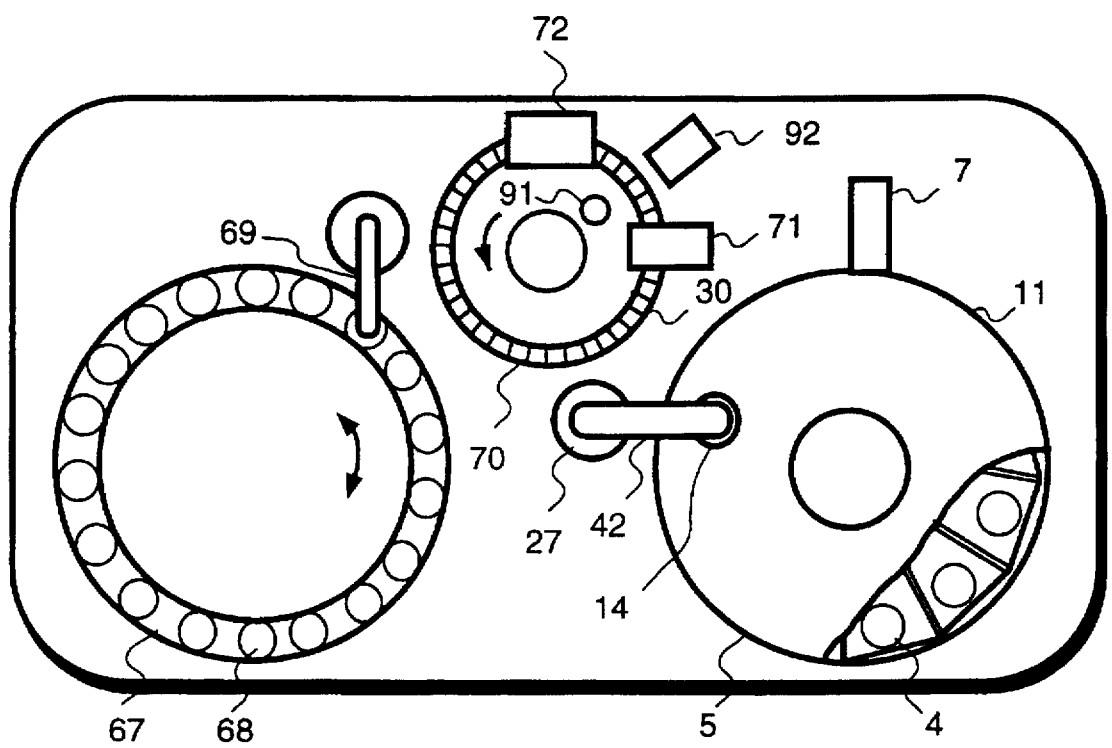
FIG. 1 is a plane view showing the overall arrangement of an automatic blood analyzer to which the present invention is applied.

FIG. 1 shows the schematic construction of an automatic blood analyzer as an embodiment to which the present invention is applied.

The analyzer has a sample disk 67, a reagent containing chamber 5, a reaction disk 70 and so on.

Located on the sample disk 67, which is rotable clockwise and counterclockwise, are a lot of sample cups 68 containing blood serum samples, originated from patients, and arranged in a circular fashion. Each of the sample cups 68 is intermittently placed at a sample sucking position. The reagent containing chamber 5 has a cover 11 which is opened when the reagent bottles 4 are loaded and unloaded. Inside the reagent containing chamber 5, there is provided a reagent disk 6 which is rotatable clockwise and counterclockwise. On the reagent disk 6, there are a lot of reagent bottles 4 arranged radially. A reaction disk 70 holds a lot of reaction containers 30 arranged in a circular fashion. The row of the reaction containers 30 are heated at 37° C. A stirring mechanism device 71 and a reactor container cleaning mechanism device 72 are operated to the reaction disk 70 with a preset period. The row of the reaction containers 30 are transferred around passing across a light beam between an incandescent light source 91 and a multi-wavelength photometer 92. Each of the blood serum samples is required to be analyzed for a plurality of analysis items depending on a corresponding disease to be inspected. A sample pipetting nozzle held by a pipetter arm 69 delivers a sample from a sample cup 68 positioned at the sample sucking position into the reaction containers 30 number of which corresponds to the number of analysis items. A reagent pipetting nozzle 42 held by a reagent pipetter arm 42 delivers a reagent corresponding to each of the analysis items from the reagent bottle 4 into the reaction container 30. A mixture of sample and reagent in the reaction container 30 is mixed by the stirring mechanism device 71 to progress a desired reaction. When the reaction container 30 passes across the light beam, optical characteristic of the reaction liquid is measured by the photometer 92. The reaction container 30 after completion of measurement is cleaned by the cleaning mechanism device 72, and the recovered reaction container is used for another sample.

In the analyzer of FIG. 1, after the reagent bottles 4 necessary for analysis items to be analyzed are contained in the reagent containing chamber 5, the reagent containing chamber 5 is closed by the cover 11 and is brought to a substantially sealed state. After closing the cover 11, a purge gas for sweeping air containing carbonic acid gas is supplied into the reagent containing chamber 5. The flow rate of the supplied purge gas is comparatively large just after closing the cover, and then decreased.

Figure 2:
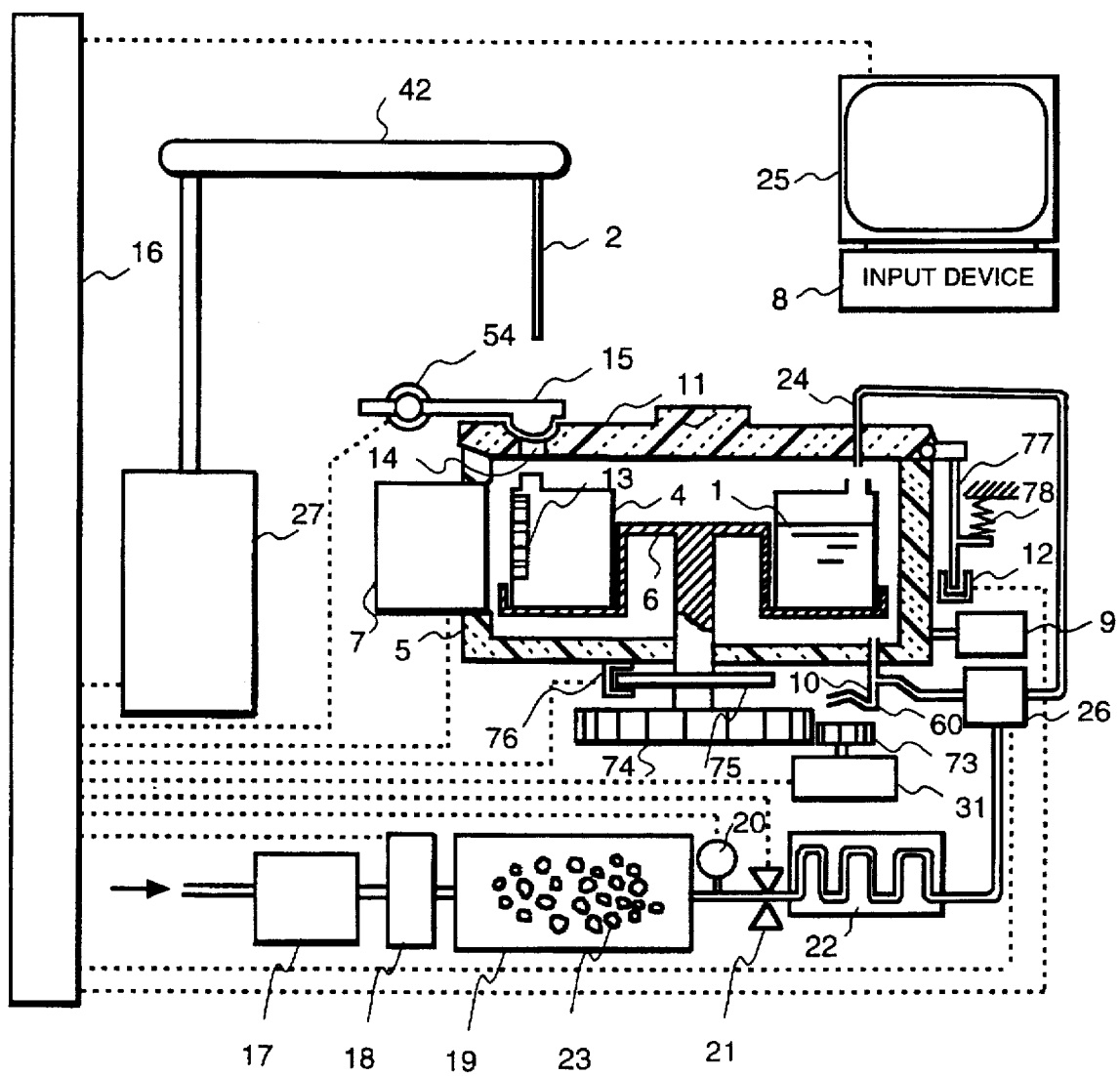
FIG. 2 is a partially sectional vertical view explaining the main portion of the embodiment of FIG. 1.

As shown in FIG. 2, the inside of the reagent containing chamber 5 is kept at a temperature lower than room temperature by a cooling device 9. Opening and closing of the cover 11 is detected by a vertical moving member 77, which is held by a spring 78, and has an end portion which moves in and out of a detector 12. Signals from the detector 12 composed of a photo-coupler, which include opening and closing of the cover 11 is transmitted to a control device 16 composed of a micro-computer. A gear 74 and a disk 75 for confirming position are attached to a rotating shaft of the reagent disk 6 arranged in the reagent containing chamber 5. The driving force of a driving device 31 operated and controlled by the control device 16 is transmitted to the gear 74 through a gear 73. Detection perforations are formed in positions on the disk 75 corresponding to the positions in which the reagent bottles 4 are placed. The position of the reagent disk 6 is performed by detecting the positions of the perforations using a position detector 76 composed of a photo-coupler.

Each of reagent bottles 4 mounted on the reagent disk 6 has an opening to allow the reagent pipetting nozzle 2 to enter through, and contains a reagent liquid 1 corresponding to each of analysis items. A bar code label 13 is attached on the outer wall of each of the reagent bottles 4. Information on name of measuring item, kind of reagent, number of production and so on displayed by bar code is read by the bar code reader 7 to be input to the control device 16. Based on the information from the bar code reader 7 and the information from the position detector 76, the control device 16 can recognize which position of the reagent disk 6 a reagent to be used for an analysis item is mounted on. In this case, a specified analysis item affected by $CO_2$, which is registered in a memory device of the control device 16 in advance, is checked with a corresponding analysis item of a reagent bottle placed on the reagent disk 6. If it is judged that a reagent bottle for the specified analysis item is placed, the control device 16 operates and control the gas supply device so as to supply a purge gas into the reagent containing chamber 5.

Instead of the input method of reading bar code on the reagent bottle, it is also possible to perform the same checking operation and the same purge gas supplying operation by key inputting, using an input device 8, analysis items corresponding to the reagent bottles and respective placing positions of the reagent bottles in regard to the reagent bottles placed on the reagent disk 6.

By providing the cover 11, which is opened for loading and unloading the reagent bottles, and the cover 15 for closing the nozzle inserting opening 14 formed on the cover 11, the inside of the reagent containing chamber 5 can be substantially sealed from the atmosphere. The cover 15 is rotated by a driving device 54 to open the opening 14 when the reagent pipetting nozzle 2 sucks the reagent liquid in the reagent bottle 4 and to close the opening 14 after the nozzle 2 is drawn up from the reagent containing chamber. Vertical movement and horizontal movement of the reagent pipetting nozzle 2 are performed by a nozzle vertical moving device 27.

The purge gas supply device comprises a filter 17 for removing dust and the like in air, a pump 18 for taking-in air, a column 19 for removing carbonic acid gas filled with carbonic acid gas absorbent 23, a pressure detector 20 for detecting pressure inside the gas flow passage, a valve 21 for controlling flow rate of the purge gas, a cooling device 22 for cooling the purge gas, a gas introducing passage 10 for introducing the purge gas through the bottom of the reagent containing chamber 5, a gas injection nozzle 24 for introducing the purge gas from the top of the reagent containing chamber 5, and a switch valve 26 for selecting the method of flowing the purge gas, that is, the purge gas is allowed to flow through both of the introducing passage 10 and the nozzle 24, or to flow through either of the introducing passage 10 and the nozzle 24. The pump 18, the flow control valve 21 and the switching valve 26 are operated and controlled by the control device 16.

In a case where a gas source not containing carbonic acid gas such as nitrogen gas is used as the purge gas instead of using air removed carbonic acid gas, a high pressure compressed nitrogen gas cylinder is connected to the flow control valve 21.

Among analysis items for blood sample, there are some analysis items using a reagent requiring oxygen. Therefore, in the apparatus of FIG. 2, air is used as the purge gas source.

Figure 3:
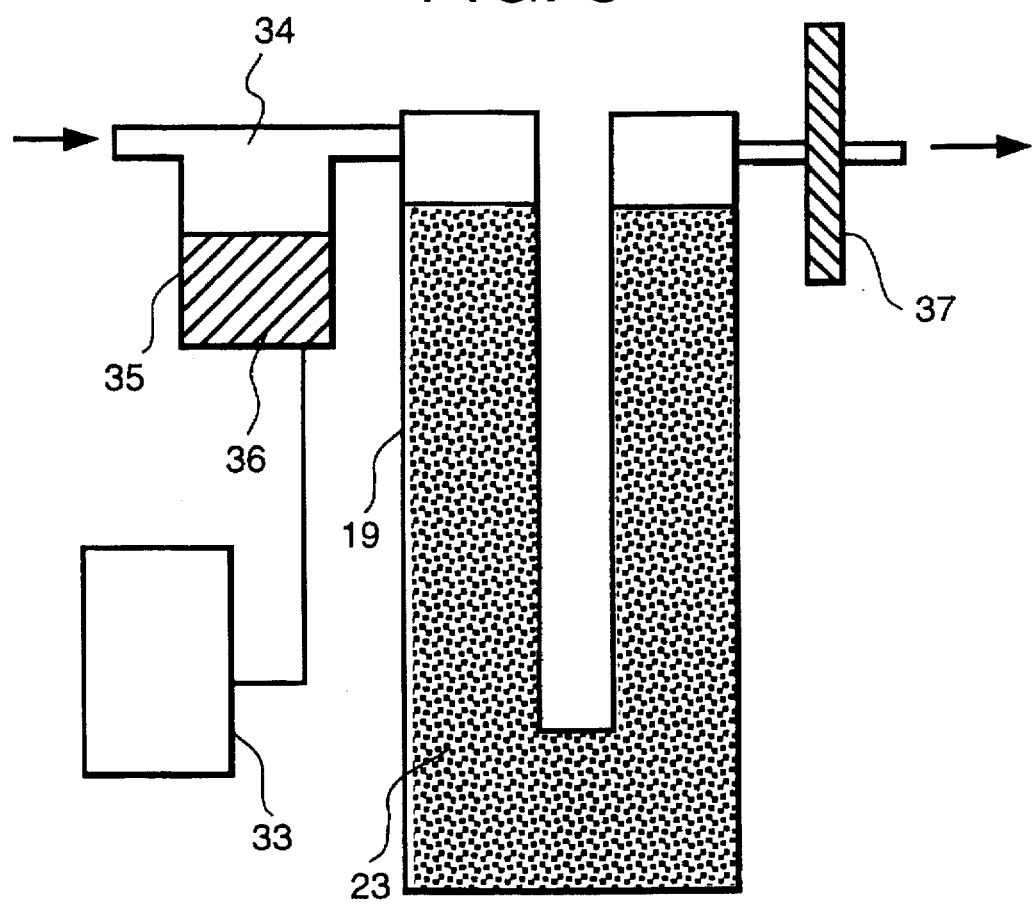
FIG. 3 is a view showing the $CO_2$ absorption column and its vicinity of FIG. 2.

FIG. 3 a view showing the carbonic acid gas absorption column 19, of FIG. 2, and its vicinity in more detail. Sodalime is filled in the column 19 as a carbonic acid gas absorbent. Sodalime is a chemical compound containing calcium hydroxide of nearly 80%, sodium hydroxide of nearly 5% and water of nearly 15%. Phosphate hydroxide may be used instead of sodium hydroxide, and further it is possible to use a chemical compound of which a part of calcium hydroxide, for example 10% of total, is exchanged by ballium hydroxide. The sodalime is preferably formed in a particle-shape, in a pellet-shape or in a disk-shape having size of 2 mm to 6 mm, since air has difficulty in flowing through when the size is too small and absorbing capability is decreased when the size is too large.

In a case of using the carbonic acid gas absorbing column 19 filled with such sodalime described above of nearly 2 liters in volume or nearly 1700 grams in weight, when atmospheric air having concentration of carbonic acid gas of 1000 ppm is used, the concentration of carbonic acid gas in the processed purge gas can be lowered to 10 ppm or less. Further, it is possible to continuously operate for 1.0 to 1.5 months with the air flow rate of approximately 2 liters per minute. It is preferable to use the column 19 in such a manner that direction of the long axes of its U-shaped pipe is held vertical, as shown in FIG. 3. A temperature and humidity regulating device 34 is connected upstream of the column 19. The regulating device 34 has a humidity regulating bottle 35 in communication with the air flow passage. Water 36 in the bottle 35 is maintained at a constant temperature of 35° C. by a temperature control device 33. By doing so, the air introduced in the column 19 has a proper humidity and proper temperature, and consequently the carbonic acid gas absorbing capability of the sodalime can be maintained constant. Downstream of the column 19, there is provided a porous air filter 37 having a perforation diameter of 10 µm for preventing sodalime powder from flowing into the column.

The time period of supplying the purge gas corresponds to operating period of the pump 18. The control device 16 monitors the operating state of the pump 18 and an accumulation value of operating time of the pump, after a column 19 is mounted, is stored in a memory of the control device 16. When the accumulation value reaches to a predetermined reference value of 700 hours, an alarm for exchanging the column is displayed on a CRT display 25 of FIG. 2. A printer or a voice device other than the display may be used as the alarm means. When the column 19 is replaced by a new one, measuring of the operating time of the pump is updated and started again.

Figure 4:
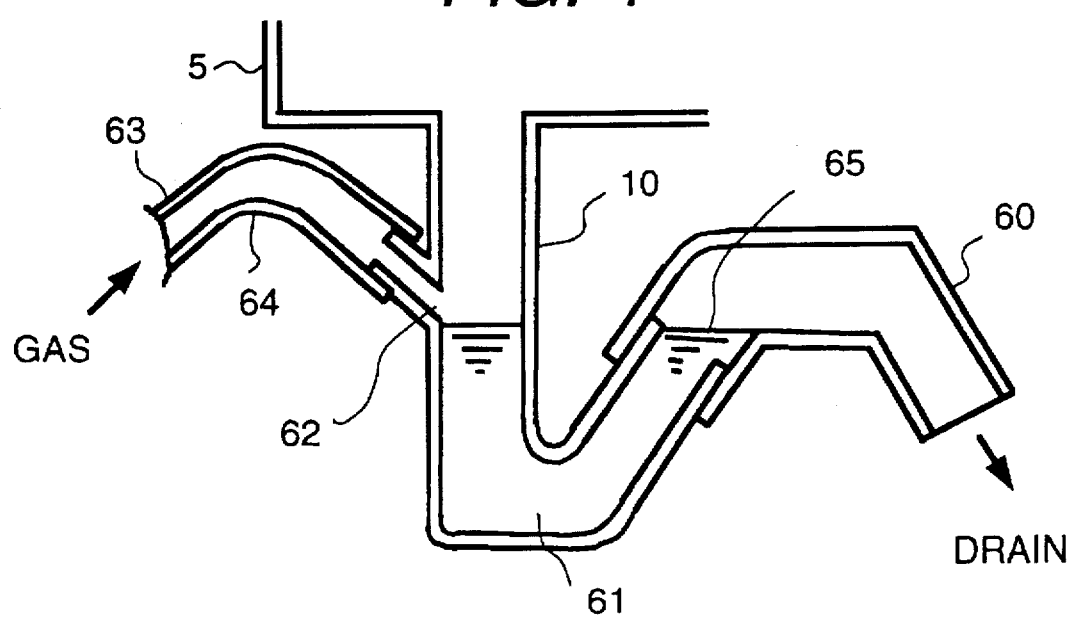
FIG. 4 is a view showing the drain and its vicinity of FIG. 2.

The gas introducing passage 10 arranged in the bottom of the reagent containing chamber 5 of FIG. 2 also serves as a drain 60. As shown in FIG. 4, the drain 60 has a bend to form a liquid trap 61. A gas flow passage 63 having a bend portion 64 is connected to an inlet 62 provided at a position slightly higher than the maximum liquid level 65 of the liquid trap 61. Since the gas flow passage 63 is inclined upward, the waste liquid cannot enter into the gas flow passage 63. Since the inside of the reagent containing chamber 5 is cooled, water condensed on the wall surface of the containing chamber 5 flows downward and is exhausted outside through the liquid trap 61. Since there is always liquid in the liquid trap 61, the purge gas introduced from the gas flow passage 63 cannot be exhausted through the drain 60.

Reagent bottles containing reagents, whose effect has been deteriorated by carbonic acid, gas are contained in the reagent containing chamber 5 of FIG. 2 together with other reagent bottles. An example of analysis items required to use such special reagents is a case of measuring bicarbonate ions, calcium, magnesium and the like. In a case where bicarbonate ions are measured, a solution containing magnesium chloride, phosphoenol pyruvate, tris-HCl buffer and NADH is used as a first reagent, and a solution containing tris-HCl buffer, phosphoenol pyruvate carboxylase and malate dihydrogenase is used as a second reagent.

In a case where bicarbonate ions are measured, it is preferable to use both of the first reagent and the second reagent under an environment without carbonic acid gas. In such a case, an analyzer used is one where two apparatuses having the same construction as the apparatus of FIG. 2 are arranged in two lines. Otherwise, by placing the first reagent and the second reagent in the reagent containing chamber 5 together, it is possible to avoid the effect of carbonic acid gas.

Figure 5:
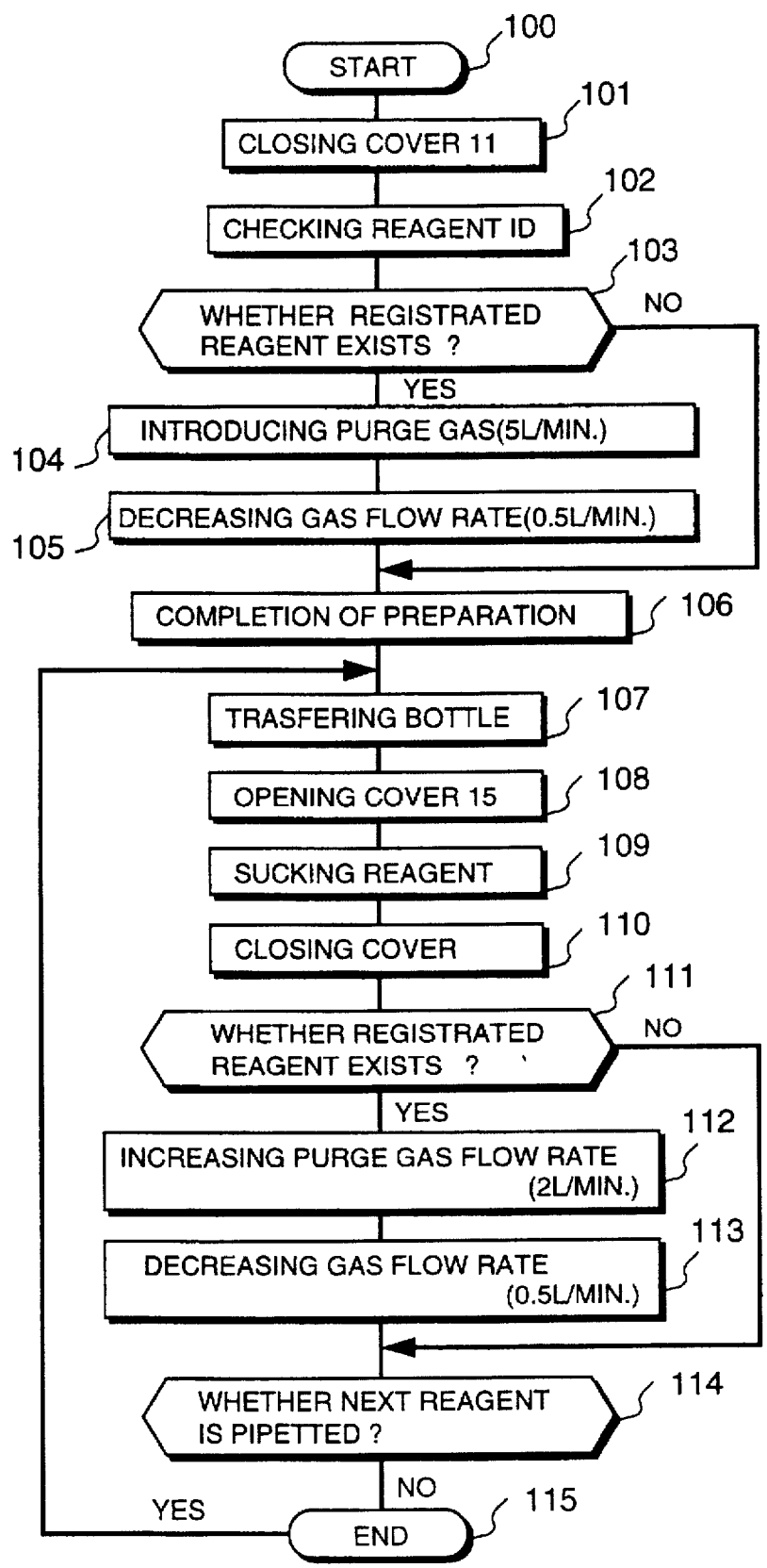
FIG. 5 is a flow chart explaining the operation of the apparatus of FIG. 2.

Operation of the apparatus of FIG. 2 will be described below, referring to FIG. 5 and FIG. 6. Before starting of Step 100 in FIG. 5, the cover 11 for loading and unloading the reagent bottles is opened, and all kinds of the reagent bottles necessary for samples to be analyzed are mounted on the reagent disk 6. In this process, each cap of the reagent bottles is removed and the reagent liquid is exposed to the atmosphere.

Before Step 100, kinds or codes of analysis items using reagents accelerated deterioration of effect by carbonic acid gas over time are key-input from the input device 8. The information is registered in a spacial analysis item table in the memory of the control device 16 composed of a microcomputer. Instead of analysis items to be registered, it is possible to input kinds or codes of reagents themselves affected by carbonic acid gas and to register them in a special reagent table.

In Step 101, as the cover 1 is closed, a detected signal by the detector is transmitted to the control device 16. Based on this, the control device 16 instructs the bar code reader 7 to read the bar code on each of the reagent bottles 4. In Step 102, the analysis item information or the reagent information read from the bar codes is related with positional information from the position detecting device 76 by the control device 16, and stored in the memory. In Step 103, the analysis item information or the reagent information read is checked against the information registered in the special reagent table. Then, it is judged whether or not any reagent bottle 4 corresponding to the registered information is contained in the reagent containing chamber 5. If there is any reagent bottle containing a reagent affected by carbonic acid gas in the reagent containing chamber, the processing proceeds to Step 104. If not, the processing proceeds to Step 106.

In Step 104, the control device 16 instructs the pump 18, the flow control valve 21 and the switching valve 26 in the purge gas supply device to operate under a condition that the opening 14 is closed with the cover 15. Thus, air removed carbonic acid gas is supplied to the reagent containing chamber 5 as a purge gas. For a certain period from starting of purge gas supply, for example, for 10 minutes, the flow control valve 21 is controlled so as to maintain the flow rate at 5 liter/minute. In this case, the switching valve 26 selects flow path so that the purge gas flows in through both of the gas introducing passage 10 and the gas injection nozzle 24.

Concentration of carbonic acid gas in out-door atmospheric air is approximately 330 ppm, and that in-door atmospheric air is 500 to 1000 ppm. Concentration of carbonic acid gas in the purge gas is kept below 50 ppm, and preferably 20 ppm. The time period from Step 104 to Step 106 is set within 30 minutes. At 10 minutes after starting the purge gas supply, the processing proceeds to Step 105. In Step 105, the control valve 21 is throttled to maintain the supplying flow rate of the purge gas at 0.5 liter/minute. The switching valve 26 selects flow path so that the purge gas flows in only through the gas introducing passage 10. This state is maintained for 5 minutes, and the processing proceeds to Step 106. In this time period, it is possible to intermittently supply the purge gas. The supply gas flow rate may be changed depending on size of the reagent containing chamber 5 and number of reagent bottles affected by carbonic acid gas.

In Step 107, a reagent bottle 4 corresponding to an analysis item instructed to be analyzed is placed at the position of the opening 14. This action is performed by controlling the driving device 31 by the control device 16 to rotate the reagent disk 6. Then, in Step 108, the driving device is operated by an instruction of the control device 16, and the opening 14 is opened by rotating the cover 15 counterclockwise as shown in FIG. 2.

In Step 109, the reagent pipetting nozzle 2 is moved downward, and inserted into the reagent liquid in the reagent bottle 4 through the opening 14. A given amount of the reagent liquid is sucked into the nozzle 2 by operation of a syringe, not shown in the figure. Then, the nozzle 2 is lifted up from the reagent containing chamber 5, and in Step 110 the opening 14 is closed with the cover 15. During the time period of Step 108 to Step 110, supply flow rate of the purge gas may be increased from the previous flow rate of 0.5 liter/minute to 2 liter/minute. The reagent sucked in the nozzle is discharged into a desired reaction bottle 30 on the reaction disk 70.

In Step 111, it is judged by the control device 16 whether or not there is any reagent affected by carbonic acid gas in the reagent containing chamber. If there is, the processing proceeds to Step 112. If not, the processing proceeds to Step 114. In Step 112, flow rate of the purge gas is increased to 2 liter/minutes for a certain period, for example, 30 seconds. By doing so, air containing carbonic acid gas is accelerated to be swept out from the reagent containing chamber 5. Then, in Step 113, flow rate of the purge gas is decreased to the previous flow rate of 0.5 liter/minutes. Operations in Step 111 and Step 112 may be performed just before Step 108.

In Step 114, it is judged whether or not any analysis item requiring the next reagent to be pipetted is instructed. If there is a sample to be analyzed next, the processing proceeds to Step 107. If there is no sample to be analyzed, the processing proceeds to Step 115, operation of the reagent pipetting is completed, and the apparatus becomes in a stand-by condition. In a case where any reagent affected by carbonic acid gas is contained in the reagent containing chamber 5, the purge gas is supplied to the reagent containing chamber 5 even when the apparatus is in a stand-by state.

Figure 6:
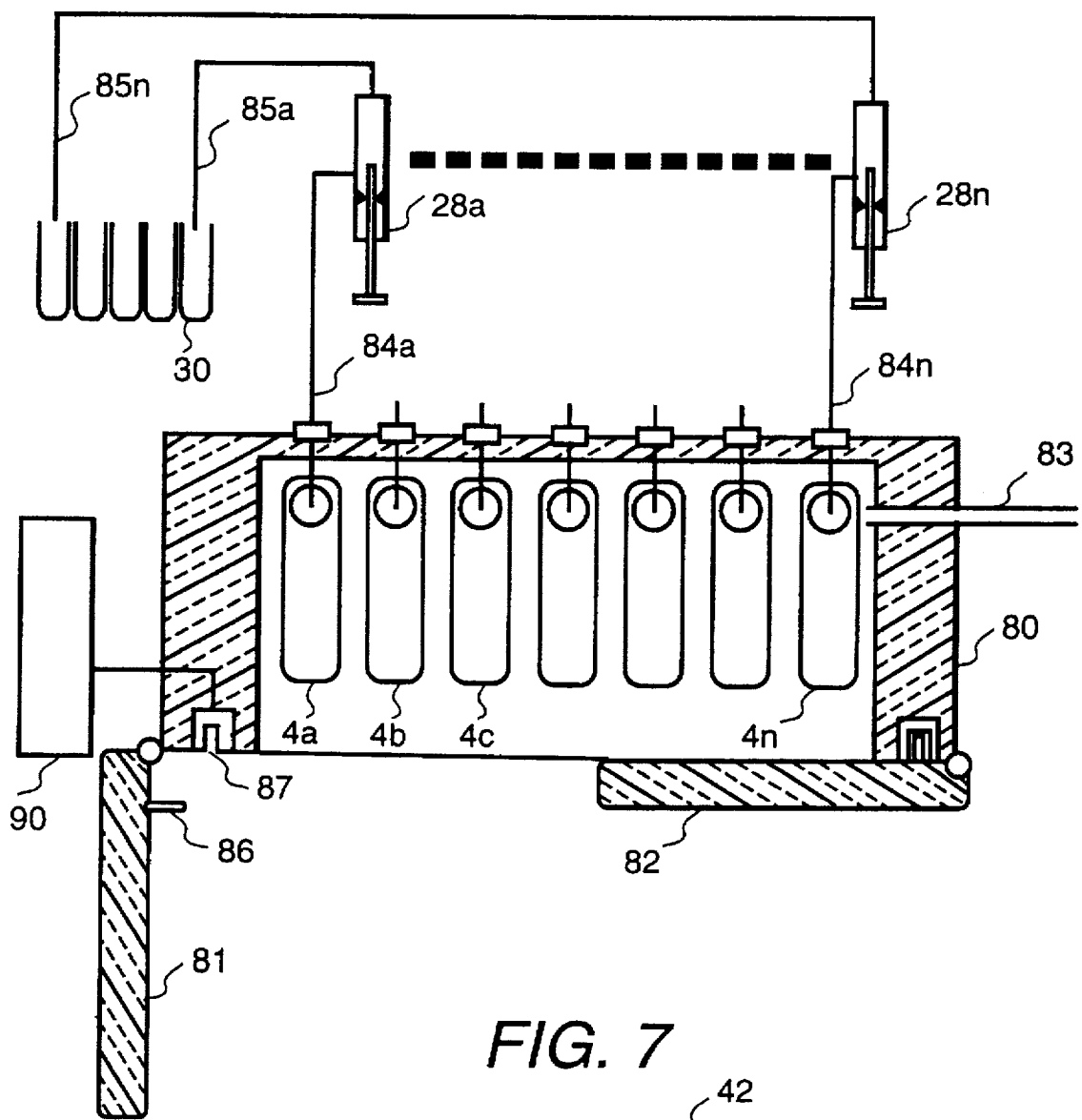
FIG. 6 is a partially sectional horizontal view showing another embodiment of a reagent containing chamber and its vicinity in accordance with the present invention.

FIG. 6 shows the main part of another embodiment of a reagent containing chamber in accordance with the present invention. The embodiment of FIG. 6 has no reagent disk in the reagent containing chamber 80. In the reagent containing chamber 80, there are placed a lot of reagent bottles 4a to 4n, and each of the reagent bottles corresponds to each of tubes 84a to 84n of which an end is inserted into the corresponding reagent bottle. The reagent liquids are delivered to reaction containers 30 allocated respective analysis items through the tubes 84a to 84n and reagent delivering tubes 85a to 85n by operation of syringes 28a to 28n.

In the box-type reagent containing chamber 80, a pair of sealing covers 81, 82 are attached. Each of the covers 81, 82 has a projection 86, and when the reagent containing chamber 80 is closed with the cover, an opening/closing detector 87 detects the projection 86 and transmits a signal indicating closing of the cover to a control device 90. Functions of a purge gas supply device, an input device 8, and a display 25 are the same as in the embodiment of FIG. 2. A gas injecting nozzle 83 for supplying purge gas is connected to the reagent containing chamber 80.

Information on reagents affected by carbonic acid gas is registered in advance, reagent information on reagent bottles contained in the reagent containing chamber 80 is checked against the registered information. Based on the checking result, the control device 90 judges whether or not there is any reagent bottle corresponding to the registered information. After the control device 90 receives both the information on existence of the corresponding reagent bottle and a signal of the cover closed form the detector 87, the control device 90 allows the purge gas to flow into the reagent containing chamber 80 through the gas injection nozzle 83.

Figure 7:
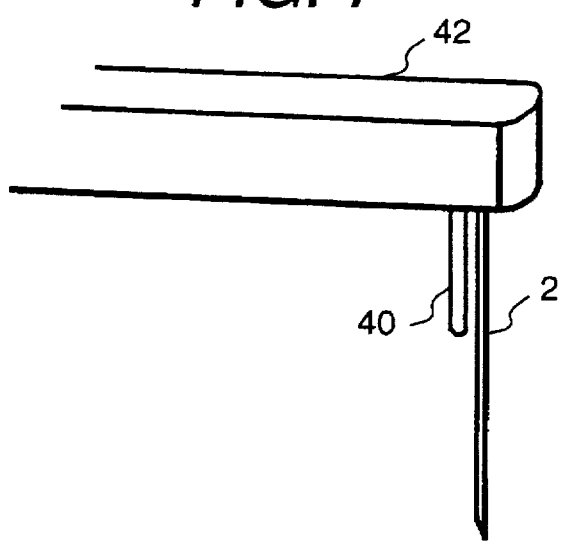
FIG. 7 is a view explaining another embodiment of a method of supplying a purge gas.

FIG. 7 shows an embodiment where a gas injection nozzle 40 is held by a pipetter arm 42 instead of the gas injection nozzle 24 of FIG. 2. In this embodiment, in addition to supplying purge gas to the reagent containing chamber 5 through the gas introducing passage 10, purge gas is injected from the gas injection nozzle 40 during reagent pipetting operation using the nozzle 2.

Without applying the present invention, calibration operation of measuring a calibrator has to be performed in the frequency of once per 2 hours in regard to an analysis item using a reagent affected by carbonic acid gas. By applying the present invention, the frequency of calibration operation is reduced to once a week. Therefore, the consumed amount of a reagent and a sample for calibration can be decreased and analysis time can be reduced.

What is claimed is:

1. An apparatus for handling a reagent having a reagent containing chamber containing a plurality of reagent bottles and a gas supply device for supplying a purge gas for sweeping air containing carbonic acid gas to said reagent containing chamber, comprising:

registering means for registering information on a reagent affected by carbonic acid gas and information on an analysis item using the reagent;

judging means for judging whether or not there is a corresponding reagent bottle to said registered information by collating information of reagent bottles contained in said reagent containing chamber with said registered information on the reagent affected by carbonic acid gas and the analysis item using the reagent; and control means for controlling said gas supply device so as to introduce said purge gas to said reagent containing chamber when said judging means judges that there is the corresponding reagent bottle.

2. An apparatus for handling a reagent according to claim 1, further comprising:

a first cover which is opened for loading the reagent bottles in said reagent containing chamber; and means for outputting a signal when said cover is closed;

said control means supplying said purge gas to said reagent containing chamber from a gas supply device on the basis of both judged information from said judging means and the cover closing signal from said control means.

3. An apparatus for handling a reagent having a reagent containing chamber containing a plurality of reagent bottles and a gas supply device for supplying a purge gas for sweeping air containing carbonic acid gas to said reagent containing chamber, comprising:

registering means for registering information on a reagent affected by carbonic acid gas and information on an analysis item using the reagent;

judging means for judging whether or not there is a corresponding reagent bottle to said registered information by collating information of reagent bottles contained in said reagent containing chamber with said registered information on the reagent affected by carbonic acid gas and the analysis item using the reagent;

control means for controlling said gas supply device so as to introduce said purge gas to said reagent containing chamber when said judging means judges that there is the corresponding reagent bottle;

a first cover which is opened for loading the reagent bottles in said reagent containing chamber;

means for outputting a signal when said cover is closed;

said control means supplying said purge gas to said reagent containing chamber from a gas supply device on the basis of both judged information from said judging means and the cover closing signal from said control means;

said first cover having an opening capable of receiving insertion of a reagent pipetting nozzle;

said apparatus for handling a reagent having a second cover for closing said opening when the reagent pipetting nozzle is outside said reagent containing chamber; and said control means increasing a flow rate of supplying said purge gas after said opening is closed with said second cover.

4. An apparatus for handling a reagent having a reagent containing chamber containing a plurality of reagent bottles and a gas supply device for supplying a purge gas for sweeping air containing carbonic acid gas to said reagent containing chamber, comprising:

registering means for registering information on a reagent affected by carbonic acid gas and information on an analysis item using the reagent;

judging means for judging whether or not there is a corresponding reagent bottle to said registered information by collating information of reagent bottles contained in said reagent containing chamber with said registered information on the reagent affected by carbonic acid gas and the analysis item using the reagent;

control means for controlling said gas supply device so as to introduce said purge gas to said reagent containing chamber when said judging means judges that there is the corresponding reagent bottle;

intake means for taking-in air;

and a column filled with an absorbent for absorbing carbonic acid gas in the taken-in air.

5. An apparatus for handling a reagent according to claim 4, further comprising:

monitoring means for monitoring an operating state of said intake means; and alarming means for alarming exchange time of said absorbent based on an accumulated value of operating time obtained by said monitoring means.

6. An apparatus for handling a reagent having a reagent containing chamber containing a plurality of reagent bottles and a gas supply device for supplying a purge gas for sweeping air containing carbonic acid gas to said reagent containing chamber, comprising:

registering means for registering information on a reagent affected by carbonic acid gas and information on an analysis item using the reagent;

judging means for judging whether or not there is a corresponding reagent bottle to said registered information by collating information of reagent bottles contained in said reagent containing chamber with said registered information on the reagant affected by carbonic acid gas and the analysis item using the reagent;

control means for controlling said gas supply device so as to introduce said purge gas to said reagent containing chamber when said judging means judges that there is the corresponding reagent bottle;

means for cooling said reagent containing chamber;

a liquid drain passage connected to a bottom of said reagent containing chamber;

a liquid trap provided in a midst of said drain passage; and an inlet port for the purge gas being connected to said drain passage between said bottom and said trap.

* * * * *